(12) United States Patent
Balchandani et al.

(10) Patent No.: US 7,966,053 B2
(45) Date of Patent: Jun. 21, 2011

(54) METHOD FOR MAGNETIC RESONANCE SPECTROSCOPIC IMAGING

(75) Inventors: Priti Balchandani, Stanford, CA (US); Daniel Spielman, Menlo Park, CA (US); John Pauly, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 818 days.

(21) Appl. No.: 11/944,739

(22) Filed: Nov. 26, 2007

(65) Prior Publication Data

US 2009/0137897 A1  May 28, 2009

(51) Int. Cl.
A61B 5/05 (2006.01)
G01N 24/00 (2006.01)
G01V 3/00 (2006.01)

(52) U.S. Cl. ........ 600/410; 436/173; 324/309; 324/312; 324/307

(58) Field of Classification Search .................. 600/410, 600/409; 324/312, 309, 307; 436/173
See application file for complete search history.

(56) References Cited

U.S. PATENT DOCUMENTS

| | | | |
|---|---|---|---|
| 5,189,371 A | | 2/1993 | Conolly et al. |
| 6,304,084 B1 * | | 10/2001 | Star-Lack et al. ............. 324/307 |
| 6,696,889 B2 * | | 2/2004 | Watanabe ..................... 329/309 |
| 2008/0272782 A1 * | | 11/2008 | Lin .............................. 324/312 |

OTHER PUBLICATIONS

Balchandani et al., "Interleaved Narrow-Band PRESS Sequence with Adiabatic Spatial-Spectral Refocusing Pulses for $^1$H MRSI at 7T", Magnetic Resonance in Medicine, vol. 59, pp. 973-979, 2008.
Bottomley P., "Spatial Localization in NMR Spectroscopy In Vivo", Annals of the New York Academy of Sciences, vol. 508, Issue 1, pp. 333-348, 1987.
Pauly et al., "Parameter Relations for the Shinnar-Le Roux Selective Excitation Pulse Design Algorithm", IEEE Trans Med Imaging, vol. 10, pp. 53-65, 1991.
Balchandani et al., "Interleaved Narrow-Band PRESS Sequence with Adiabatic Spatial-Spectral Refocusing Pulses for $^1$H MRSI at 7T", Magn Reson Med, proof—unpublished.
Choi et al., "Single-Shot Two-Echo Technique for Simultaneous Measurement of GABA and Creatine in the Human Brain in Vivo", Magn Reson Med, vol. 51, pp. 1115-1121, 2004.
Geppert et al., "Fast 1H spectroscopic imaging using steady state free precession and spectral-spatial RF pulses", Magn Reson Mater Phy, vol. 19, pp. 196-201, 2006.

* cited by examiner

*Primary Examiner* — Long V Le
*Assistant Examiner* — Helene Bor
(74) *Attorney, Agent, or Firm* — Beyer Law Group LLP

(57) ABSTRACT

A method for performing spectroscopy using an interleaved readout for at least two species. A $B_0$ field is applied. A first spatial-spectral (SPSP) position resolved spectroscopy sequence (PRESS) excitation with a sufficiently narrow band to excite a first species without exciting a second species is applied. A first readout that measures the first species is performed. A second SPSP PRESS excitation with a sufficiently narrow band to excite the second species without exciting the first species is applied. A second readout that measures the second species is performed.

20 Claims, 9 Drawing Sheets

Water Image

B₁ field normalized to coil isocenter (a.u.)

B₀ Shift (Hz)

US 7,966,053 B2

METHOD FOR MAGNETIC RESONANCE SPECTROSCOPIC IMAGING

STATEMENT REGARDING FEDERALLY SPONSORED RESEARCH OR DEVELOPMENT

This invention was made with Government support under contract RR09784 awarded by the National Institutes of Health. The Government has certain rights in invention.

BACKGROUND OF THE INVENTION

This invention relates generally to magnetic resonance imaging (MRI), and more particularly the invention relates to spectroscopic MRI.

Magnetic resonance imaging (MRI) requires placing an object to be imaged in a static magnetic field ($B_0$), exciting nuclear spins in the object with a RF magnetic field ($B_1$), and then detecting signals emitted by the excited spins as they precess within the magnetic field ($B_0$). Through the use of magnetic gradient and phase encoding of the excited magnetization, detected signals can be spatially localized in three dimensions. MR Spectroscopic Imaging combines spectroscopy with MRI to yield a grid of spectra covering the volume of interest.

SUMMARY

A manifestation of the invention provides a method for performing spectroscopy using an interleaved readout for at least two species. A $B_0$ field is applied. A first spatial-spectral (SPSP) position resolved spectroscopy sequence (PRESS) excitation with a sufficiently narrow band to excite a first species without exciting a second species is applied. A first readout that measures the first species is performed. A second SPSP PRESS excitation with a sufficiently narrow band to excite the second species without exciting the first species is applied. A second readout that measures the second species is performed.

In another manifestation of the invention provides a computer implemented method. A $B_0$ field is applied. For a plurality of cycles a first spatial-spectral (SPSP) position resolved spectroscopy sequence (PRESS) excitation with a sufficiently narrow band to excite a first species without exciting a second species is applied, a first readout is performed that measures the first species, a second SPSP PRESS excitation with a sufficiently narrow band to excite the second species without exciting the first species is applied, and a second readout is performed that measures the second species. The first SPSP PRESS excitation comprises a SPSP 90° pulse, a first adiabatic SPSP 180° pulse, and a second adiabatic SPSP 180° pulse, wherein the SPSP 90° and the first and second adiabatic SPSP 180° pulses each have a spectral profile centered on the resonant frequency for exciting the first species and a spectral bandwidth sufficiently narrow to avoid exciting the second species. The second SPSP PRESS excitation comprises a SPSP 90° pulse, a first adiabatic SPSP 180° pulse, and a second adiabatic SPSP 180° pulse, wherein the SPSP 90° and the first and second adiabatic SPSP 180° pulses each have a spectral profile centered on the resonant frequency for exciting the second species and a spectral bandwidth sufficiently narrow to avoid exciting the first species.

In another manifestation of the invention a magnetic resonance imaging apparatus is provided. A magnetic resonance imaging excitation and detection system is provided. A controller is electrically connected to the magnetic resonance imaging excitation and detection system. The controller comprises a display, at least one processor, and computer readable media. The computer readable media comprises computer readable code for applying a $B_0$ field, computer readable code for applying a first spatial-spectral (SPSP) position resolved spectroscopy sequence (PRESS) excitation with a sufficiently narrow band to excite a first species without exciting a second species, computer readable code for performing a first readout that measures the first species, computer readable code for applying a second SPSP PRESS excitation with a sufficiently narrow band to excite the second species without exciting the first species, computer readable code for performing a second readout that measures the second species, computer readable code for generating a spectroscopic image for the first species and the second species from the first and second readouts, and computer readable code for displaying the spectroscopic image on the display.

The invention and objects and features thereof will be more readily apparent from the following detailed description and appended claims when taken with the drawings.

DETAILED DESCRIPTION OF ILLUSTRATIVE EMBODIMENTS

Overview

Figure 1A:
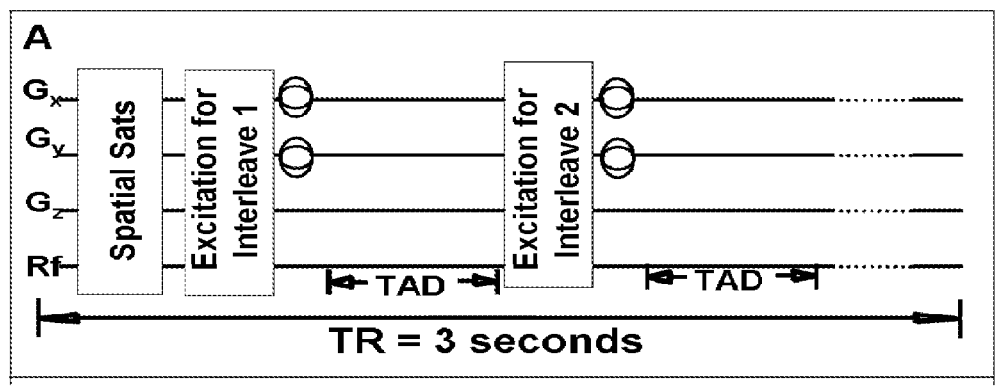
FIGS. 1A-B illustrate an interleaved narrow-band SPSP pulse sequence with a first interleaf exciting Spectral Band 1 (centered between Cho and Cre resonances) and a second exciting Spectral Band 2 (centered on the NAA resonance)

Proton magnetic resonance spectroscopic imaging ($^1$H MRSI) is a useful technique for measuring metabolite levels in vivo, with Choline (Cho), Creatine (Cr) and N-Acetyl-Aspartate (NAA) being the most prominent MRS-detectable brain biochemicals. $^1$H MRSI at very high fields, such as 7 T, offers the advantages of higher SNR and improved spectral resolution. However, major technical challenges associated with high-field systems, such as increased $B_1$ and $B_0$ inhomogeneity as well as chemical shift localization (CSL) error, degrade the performance of conventional $^1$H MRSI sequences. To address these problems, an embodiment of the invention uses a Position Resolved Spectroscopy (PRESS)

sequence with adiabatic spatial-spectral (SPSP) refocusing pulses, to acquire multiple narrow spectral bands in an interleaved fashion. The adiabatic SPSP pulses provide magnetization profiles that are largely invariant over the 40% $B_1$ variation measured across the brain at 7 T. Additionally, there is negligible CSL error since the transmit frequency is separately adjusted for each spectral band. In vivo $^1$H MRSI data was obtained from the brain of a normal volunteer using a standard PRESS sequence and the interleaved narrow-band PRESS sequence with adiabatic refocusing pulses. In comparison with conventional PRESS, the inventive approach generated high quality spectra from an appreciably larger region of interest and achieved higher overall SNR.

Proton magnetic resonance spectroscopic imaging ($^1$H-MRSI) offers a non-invasive method for the identification, visualization, and quantification of specific brain biochemical markers and neurotransmitters, the assessment of abnormalities in injured or diseased brain tissue, the longitudinal monitoring of degenerative diseases, and the early evaluation of therapeutic interventions. The most prominent in vivo $^1$H MRS-detectable brain metabolites are N-acetyl aspartate (NAA, found largely in neuronal cell bodies, dendrites, and axons, and hence commonly used as neuronal marker), choline containing compounds (Cho, largely constituents of phospholipid metabolism and usually interpreted as an indicator of cell membrane synthesis or degradation) and creatine/phosphocreatine (Cr, a measure of high-energy metabolic processes.

Technically, in vivo $^1$H-MRS of the brain is complicated by many factors, including low signal-to-noise ratio (SNR), large water and lipid resonances, magnetic field inhomogeneities, and overlapping metabolite peaks. The clearly identified need to improve sensitivity and resolution has been a primary driving force behind the development of ultrahigh-field human scanners (e.g., 7 T). $^1$H MRSI at 7 T offers the advantages of increased SNR, which may be used to reduce scan times or improve spatial resolution, and increased peak separation, which results in improved spectral resolution. However, $B_1$ inhomogeneity, $B_0$ inhomogeneity and chemical shift localization (CSL) errors significantly limit the performance of high-field in vivo human spectroscopic imaging. Approximately 40% $B_1$ variation was measured across the adult human head in our 7 T GE whole body magnet. The conventional Position Resolved Spectroscopy (PRESS) sequence, as discussed by Bottomley P., in "Spatial Localization in NMR Spectroscopy In Vivo," Ann NY Acad. Sci 1987; 508:333, utilizes linear-phase Shinnar-Le Roux (SLR), excitation and refocusing pulses that are sensitive to changes in $B_1$ as discussed by Pauly J, Le Roux P, Nishimura D, Macovski A., in "Parameter Relations for the Shinnar-Le Roux Selective Excitation Pulse Design Algorithm," IEEE Trans Med Imaging 1991; 10:53. Additionally, CSL error scales with field resulting in significant spatial misregistration between metabolites.

In order to address the issue of $B_1$ and $B_0$ inhomogeneity as well as CSL error, an interleaved narrow-band PRESS sequence with adiabatic spatial-spectral (SPSP) refocusing pulses is provided by an embodiment of the invention. The sequence acquires two separate spectral passbands, one for Cho and Cre and a second for NAA, within one TR. Each band is acquired using a linear-phase SPSP 90° pulse followed by two phase-matched narrow-band adiabatic SPSP 180° pulses for volume localization. The sequence has a number of important advantages. First, the 180° refocusing pulses are adiabatic, thus gaining insensitivity to $B_1$ inhomogeneities. Second, each spectral band has a bandwidth of 285 Hz, making the sequence robust to peak shifts due to the $B_0$ inhomogeneity. Finally, shifting the center frequency for each narrow-band excitation virtually eliminates chemical shift misregistration errors.

Methods

Overall Pulse Sequence

Figure 1B:
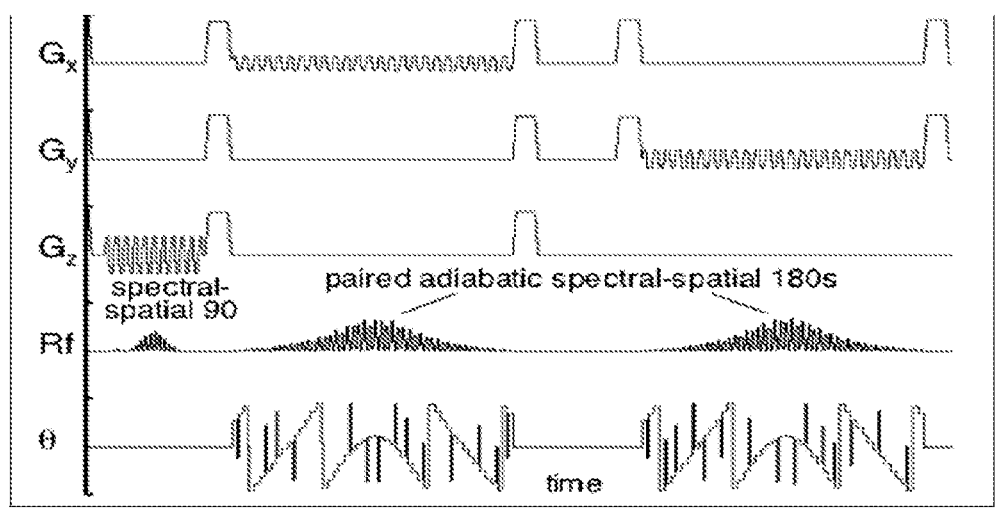

The overall $^1$H MRSI pulse sequence provided by an embodiment of the invention is shown in FIG. 1A, which illustrates an interleaved narrow-band SPSP pulse sequence with a first interleaf exciting Spectral Band 1 (centered between Cho and Cre resonances) and a second exciting Spectral Band 2 (centered on the NAA resonance). The timing parameters for the sequence are readout duration (TAD) =512 ms, TE=90 ms, and TR=3 s. The long TR's required at 7 T, to reduce warming, leave room for the insertion of a third interleaf. One SPSP 90° pulse followed by two adiabatic SPSP 180° pulses with a narrow spectral bandwidth of 285 Hz are used to individually excite a single or a group of closely spaced metabolites in an interleaved fashion. FIG. 1B shows the excitation RF and gradient waveforms used to excite each interleaved frequency band. Interleaving allows excitation of a large spectral range without an increase in scan time. The sequence works in a manner similar to multi-slice imaging, but with spectral bands instead of slices. Using adiabatic SPSP refocusing pulses with a narrow spectral bandwidth centered on the chosen metabolite resonance for a given interleaf allows adiabatic refocusing for a range of $B_1$ values as well as immunity to $B_0$ shifts for a given RF peak amplitude limit. A SPSP 90° pulse designed to have the same 2D spatial-spectral profile as the adiabatic SPSP 180° pulses is used for excitation. Since the transmit frequency is set to the center of each interleaved spectral band, there is negligible relative shift between the excited volumes for different metabolites. Thus, this approach provides greater immunity to $B_1$ and $B_0$ inhomogeneity, while virtually eliminating chemical shift localization error.

Pulse Design

All pulses used in the sequence were spatial-spectral to take advantage of the significantly increased spatial bandwidth, and hence reduced chemical shift misregistration, offered by these pulses. Since standard SPSP pulses are still susceptible to the significant $B_1$ variation at 7 T, adiabatic SPSP 180° pulses were used to provide some immunity to $B_1$ variations as well as CSL errors. Such adiabatic pulses are described in Conolly et al. U.S. Pat. No. 5,189,371, which is incorporated by reference. The two adiabatic refocusing pulses have compensating nonlinear spectral phase profiles, significantly reducing both the required peak and average RF power. Due to the unavailability of low power, slice-selective adiabatic excitation pulses, a standard SPSP 90° was used.

Adiabatic SPSP 180° Pulse Design

The adiabatic SPSP 180° pulse was designed by first creating an adiabatic sech/tan h pulse using Eqns. 1 and 2 for the amplitude and frequency modulation functions respectively.

$$A(t)=A_0 \mathrm{sech}(\beta t) - T/2 \leq t \leq T/2 \quad (1)$$

$$\Delta\omega(t)=-\mu\beta \tan h(\beta t) - T/2 \leq t \leq T/2 \quad (2)$$

where the maximum $B_1$ field $A_0$=11 µT, the modulation angular frequency $\beta$=300 rad/s, the bandwidth determining dimensionless parameter $\mu$=3.2, and the pulse duration T=24 ms.

Figure 2A:
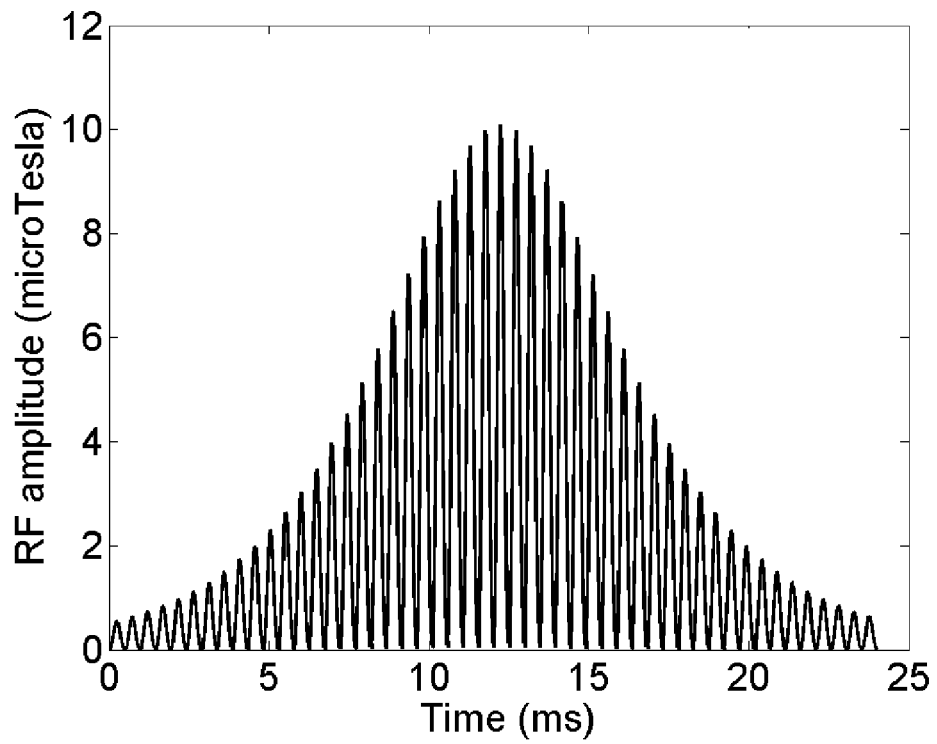
FIGS. 2A-B show an adiabatic SPSP 180° RF pulse used for refocusing.
Figure 2B:
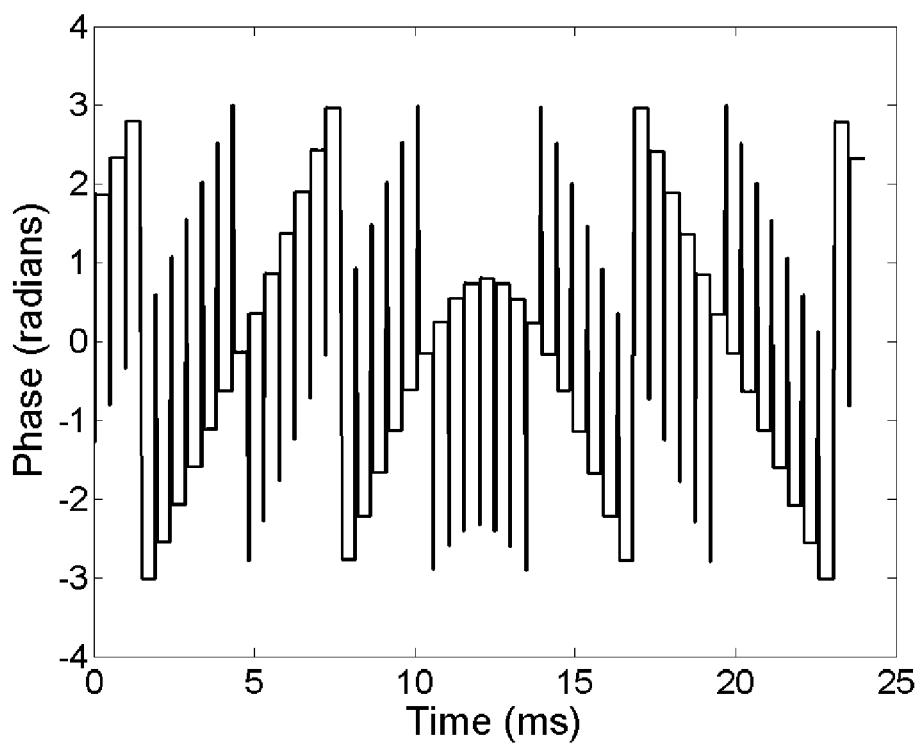

The resultant pulse had a spectral bandwidth of 285 Hz to account for metabolite shifts of ±0.475 ppm due to $B_0$ inhomogeneities at 7 T. The pulse was then subsampled with an optimal trade off between sideband distance and minimum slice thickness yielding 50 samples. The spectral sidebands had to be placed at a sufficient distance away from the main passband such that NAA didn't get excited in the first acquisition. The final adiabatic SPSP pulse was comprised of 50 conventional small tip-angle subpulses scaled by the sampled values of the adiabatic sech/tan h envelope. The resultant separation between the main passband and sidebands was ±1.9 kHz. The opposing sidebands were located at ±950 Hz. This separation was large enough to prevent erroneous excitation of metabolites meant for the next interleaf. FIG. 2A shows the magnitude and FIG. 2B shows the phase of the final 24 ms adiabatic SPSP 180° RF pulse used for refocusing. The peak $B_1$ value of the pulse is well below the limit of the 7 T RF amplifier, which in this example is 17 μT. The pulse is played in conjunction with an oscillating gradient waveform.

Figure 3A:
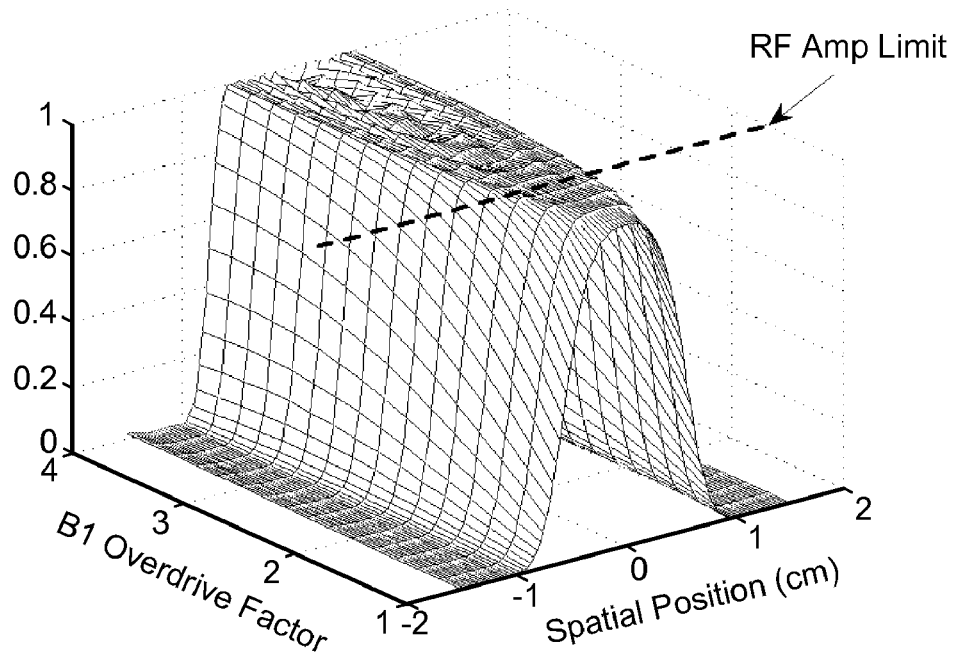
FIG. 3A shows a simulated spatial profile is shown for an adiabatic SPSP 180° pulse for a range of $B_1$ overdrive factors above adiabatic threshold.
Figure 3B:
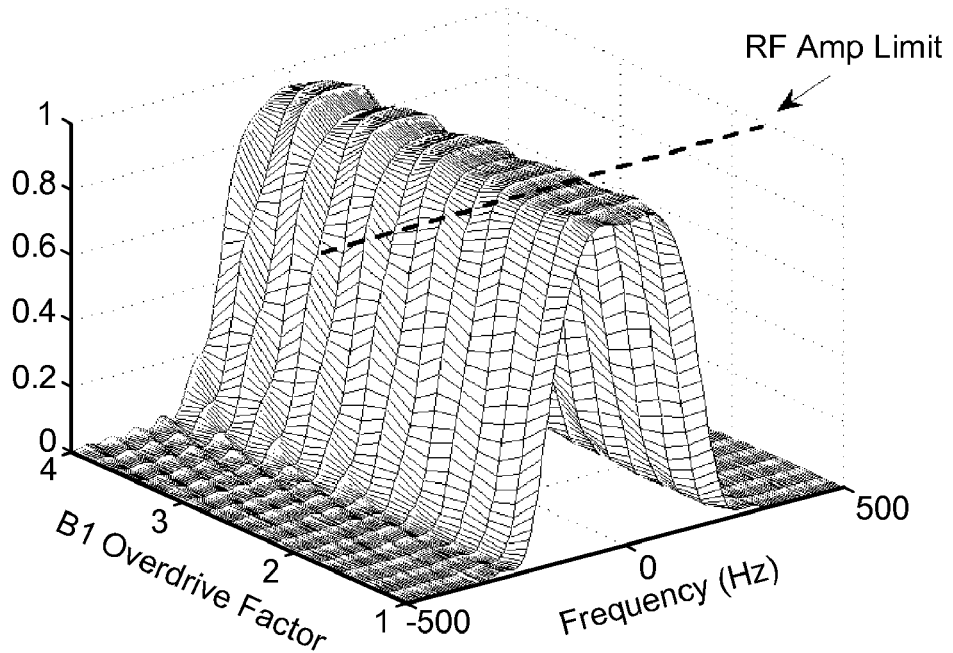
FIG. 3B shows a main spectral passband of the pulse over the same range of $B_1$ overdrive factors.

The adiabaticity of the spatial and spectral magnetization profiles of the pulse was verified through simulations. In FIG. 3A, the simulated spatial profile is shown for the adiabatic SPSP 180° pulse for a range of $B_1$ overdrive factors above adiabatic threshold. If the nominal $B_1$ is set to be at the adiabatic threshold, the pulse may be overdriven by 60% (i.e. an overdrive factor of 1.6) before reaching the 17 μT RF peak amplitude limit for our 7 T RF amplifier. In order to ensure that the pulses are insensitive to the $B_1$ variation observed at 7 T, the adiabatic threshold for the pulses needs to be low enough to allow at least a 40% overdrive factor without exceeding the RF peak amplitude limit of 17 μT. An increase in spatial selectivity with increasing $B_1$ is noticeable in FIG. 3A. However, if the pulse is overdriven by factors above 2.5, well beyond the RF peak amplitude limit, there is some degradation in the spatial profile at the center. FIG. 3B shows the main spectral passband of the pulse over the same range of $B_1$ overdrive factors. The spectral profile stays invariant over a 60% increase in $B_1$, at which point the RF amplifier limit (17 μT) is reached. Beyond an overdrive factor of 2.5, there is some variation in passband behavior and increase in stopband ripple.

Linear-Phase SPSP 90° Pulse Design

A linear-phase SPSP 90° pulse was designed to have the same spectral profile as the adiabatic SPSP 180° pulse. Pulse design was similar to the 180° pulse except a linear-phase SLR envelope was used instead of a sech/tan h adiabatic envelope.

Interleaving

In principle, the sequence could have been designed without interleaves, with one excitation covering the entire spectral of range of interest. However, simulations showed that the adiabatic SPSP refocusing pulses reached the 17 μT peak RF amplitude limit of our 7 T scanner at a spectral bandwidth of approx 500 Hz. For a non-interleaved sequence, this limited spectral passband, combined with the increased spectral separation at 7 T would result in metabolite signal loss due to peaks shifts caused by $B_0$ inhomogeneity. In addition, operating the pulses at the peak RF amplitude limit leaves insufficient RF power to overdrive the pulses and maintain the adiabatic condition during excitation. Dividing the spectral range of interest into several interleaved narrow bands enables greater immunity to $B_0$ shifts and $B_1$ variations without increased scan time. The technique is particularly advantageous for reduction of CSL errors, as the transmit frequency is shifted to the center of each interleaved band, yielding negligible relative spatial shift.

Figures 4A, 4B, 4C:
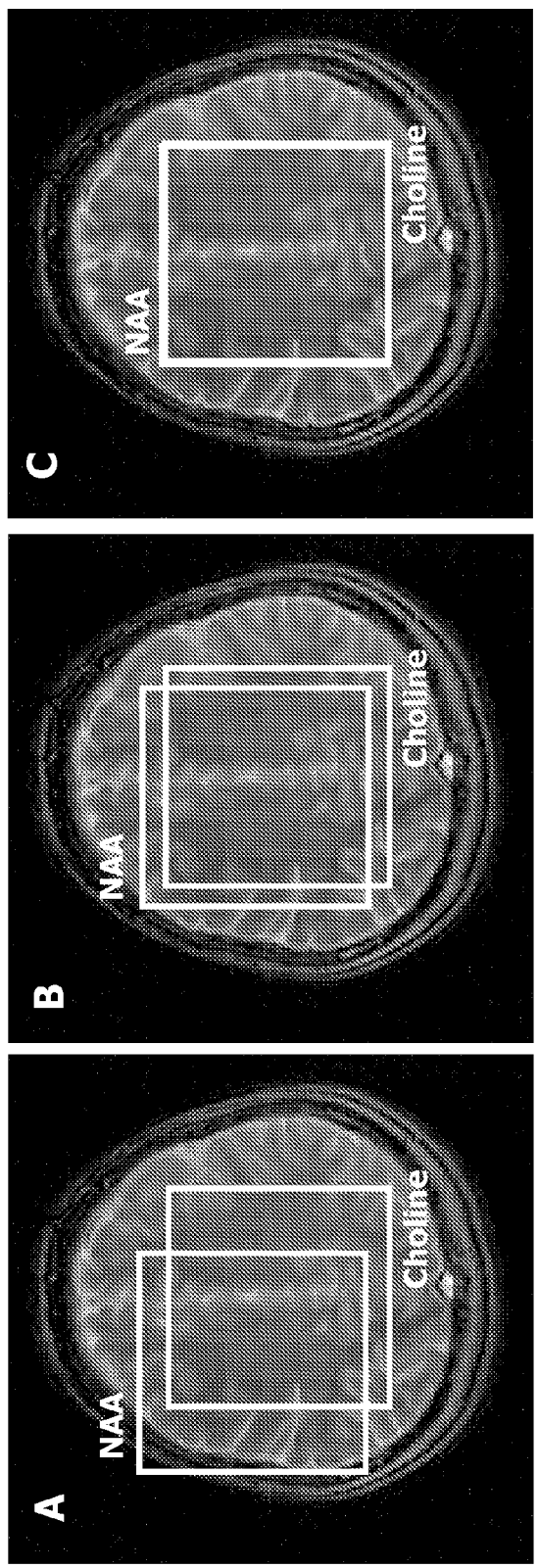
FIGS. 4A-C shows the relative shift between the excited volumes for NAA and Cho for the three sequences at 7 T.

Chemical shift localization error was calculated and compared for conventional PRESS, PRESS using SPSP pulses and the interleaved narrow-band PRESS sequence with adiabatic SPSP refocusing pulses. FIGS. 4A-C shows the relative shift between the excited volumes for NAA and Cho for the three sequences at 7 T. For conventional PRESS shown in FIG. 4A, linear-phase SLR pulses with limited spatial bandwidth are used to excite along the in-plane dimension resulting in significant shift between the selected PRESS boxes for NAA and Cho. Typically the 90° excitation pulse is used to localize along at least one of the in-plane dimensions (in FIG. 4A, the anterior-posterior dimension) resulting in less severe CSL error along that dimension. FIG. 4B shows the significant reduction in CSL error when SPSP pulses, which have higher spatial bandwidth, are used instead of conventional SLR pulses in the PRESS excitation with SPSP 180° pulses. FIG. 4C shows the nearly coincident excited volumes when an interleaved narrow-band PRESS sequence with adiabatic SPSP 180° pulse approach is used. CSL error is mostly but not completely eliminated due to the small spectral separation (0.2 ppm) between the Cho and Cre resonances.

Final Pulse Sequence Parameters

In the sequence, as shown in FIG. 1, volume excitation for each interleaved band was achieved by the SPSP 90° pulse followed by two adiabatic SPSP 180° pulses. This was repeated within the same TR and the two echoes acquired were from passbands centered on Cho+Cre and NAA respectively. Even with a 512 ms readout, both narrow-band acquisitions can easily be interleaved into the 3 s TR window used for the overall sequence timing. A long TR is used to accommodate the long metabolite $T_1$'s at 7 T and to stay within SAR limits. The 3 s TR affords sufficient time to interleave a third water acquisition as a reference for quantification. A 90 ms echo time was chosen as a compromise between reducing T2-induced signal losses and allowing sufficient time for the three spectral-spatial RF pulses.

Figure 5A:
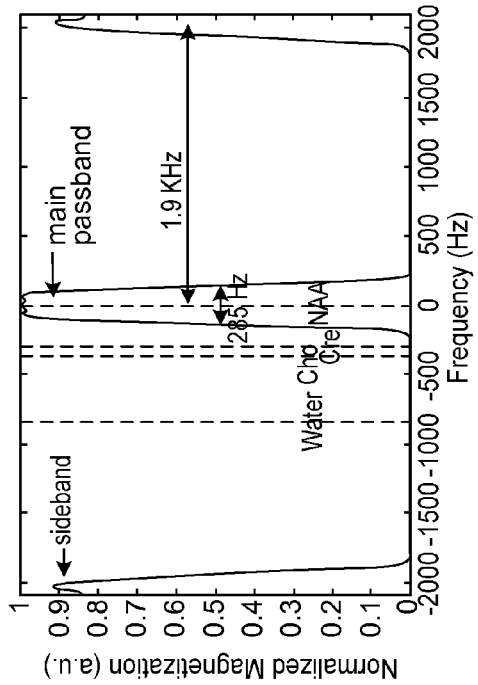
FIGS. 5A-D shows simulations of the magnetization profiles for the final echo acquired at readout following the three 90°-180°-180° pulses.
Figure 5B:
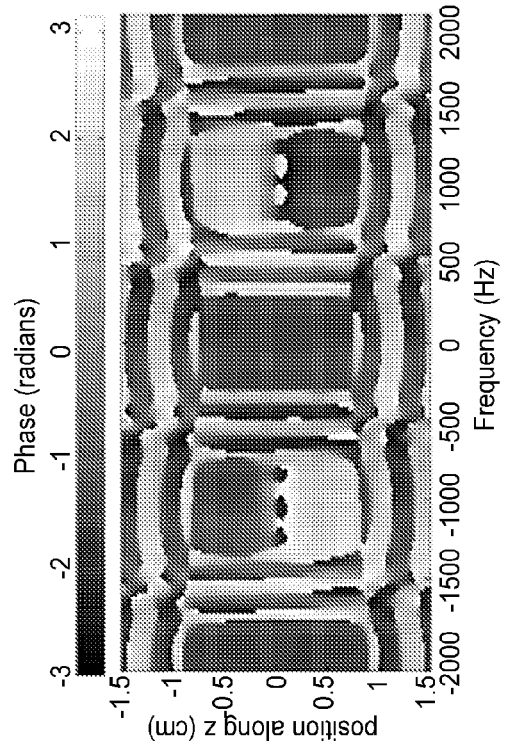
Figure 5C:
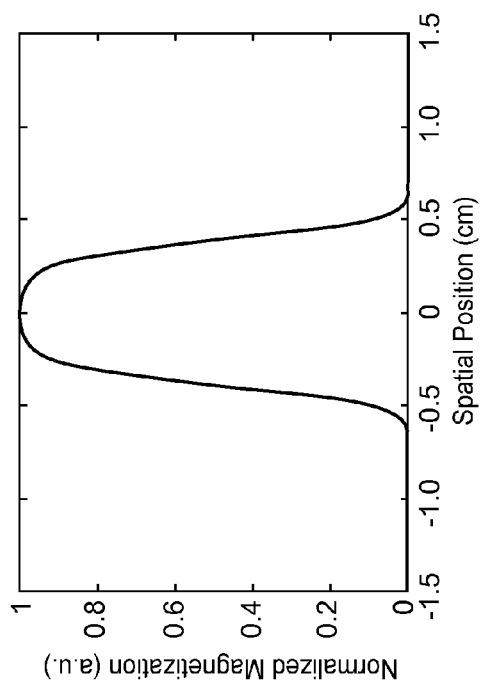
Figure 5D:
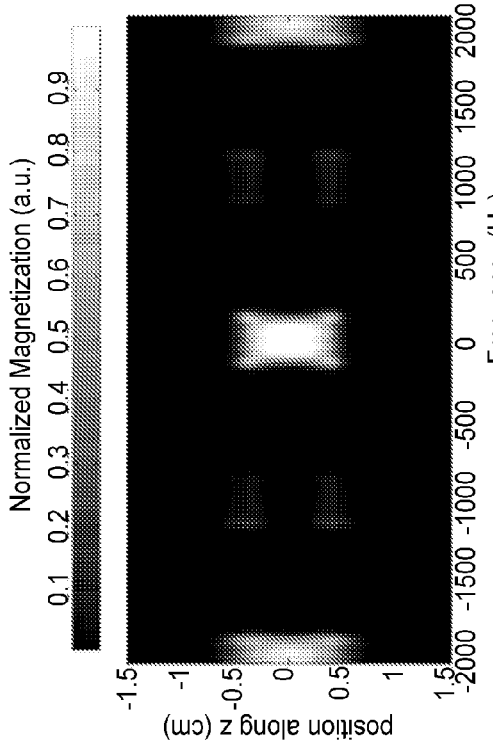

FIGS. 5A-D shows simulations of the magnetization profiles for the final echo acquired at readout following the three 90°-180°-180° pulses. FIG. 5A shows the spatial profile of the final echo for a 0.75 cm slice. The spectral profile for the final echo, showing the main spectral passband with a bandwidth of 285 Hz and sidebands located at ±1.9 kHz, is shown in FIG. 5B. All pulses were designed so that the frequency separation between the main passband band sidebands was large enough not to erroneously excite metabolites designated for the next interleaf. Therefore the sidebands are placed far enough from the main passband to not overlap with other metabolites, which in this example is +/−1.9 kHz. Metabolite and water resonance frequencies are depicted for the case of the first interleaf, with the spectral band centered between the closely spaced Cho and Cre resonances. Dashed lines show resonant frequencies for metabolites when the main spectral passband is centered on Cho and Cre. The main passband, sidebands, as well as faint opposing sidebands are visible in the 2D spatial-spectral profile shown in FIG. 5C, which shows a 2D spatial-spectral magnitude profile for pulse, showing selectivity in both space and frequency. The opposed sidebands visible at ±950 Hz are also located such that there is not spectral interference between interleaves When the main spectral passband is centered between Cho and Cre, the sidebands shown in FIGS. 5B & C do not overlap with the water and NAA resonances ensuring mutual exclusivity of the interleaved spectral bands. Similarly, the Cho, Cre and water resonances are not affected when the main spectral band is centered on NAA. The spatial phase of the profile at the final echo is determined by the spatial subpulses. Linear-phase subpulses were used for all SPSP pulses, hence, the spatial phase of the final echo is linear. Because the use of a pair of identical adiabatic SPSP 180° pulses results in the refocusing of their nonlinear spectral phase, the spectral phase at the final echo is linear as well. The 2D phase profile of the final echo is depicted in FIG. 5D, which shows the 2D spatial-spectral phase profile demonstrating that flat phase for the main passband is achieved.

The sequence was tested in vivo by exciting a single slice through the brain of a normal volunteer and comparing the results to those obtained using a conventional PRESS sequence. The scans were performed on our 7 T scanner (Echospeed whole-body magnet; GE Healthcare, Waukesha, Wis., USA) using a standard GE volume head coil. The acquisition parameters for the $^1$H MRSI scan were: Slice thickness=1.5 cm, FOV=18×18 cm, matrix size=12×12 (5×5 voxels within the PRESS box), voxel volume=3.4 cc, TE/TR=90/3000 ms, NEX=1 and scan time=7:10 min. $B_1$ and $B_0$ maps of the imaged slice were also obtained.

Results

Figures 6A, 6B, 6C:
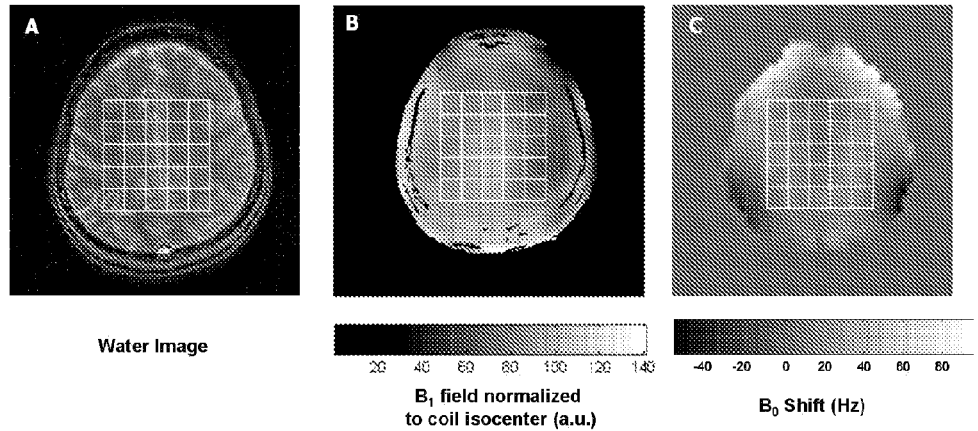
FIGS. 6A-C are images of a 1.5 mm slice of a normal human brain for which $^1$H MRSI data was obtained at 7 T with a 5×5 spectral grid within the prescribed PRESS box.

FIGS. 6A-C are images of a 1.5 mm slice of a normal human brain for which $^1$H MRSI data was obtained at 7 T with a 5×5 spectral grid within the prescribed PRESS box. FIG. 6A shows the image of the single slice through the brain of a normal volunteer scanned at 7 T. $^1$H MRSI data were obtained with a conventional PRESS sequence and the interleaved narrow-band PRESS sequence with adiabatic SPSP refocusing pulses. The PRESS box and spectral grid location for both $^1$H MRSI experiments are shown on the image in FIG. 6A. The measured $B_1$ map for the same slice, acquired using a double-angle method, can be seen in FIG. 6B. An approximate 40% reduction in $B_1$ from the center to the periphery of the brain is evident. The $B_0$ map in FIG. 6C was obtained after first and second order shimming was used to optimize the $B_0$ homogeneity (17.75 Hz RMS, 180 Hz peak-to-peak). The location of the spectral grid on the images show the expected $B_1$ and $B_0$ changes between voxels. Changes in $B_0$ over the region of interest stay well below the width of the spectral band of the SPSP pulses used in an embodiment of the invention.

Figures 6D, 6E:
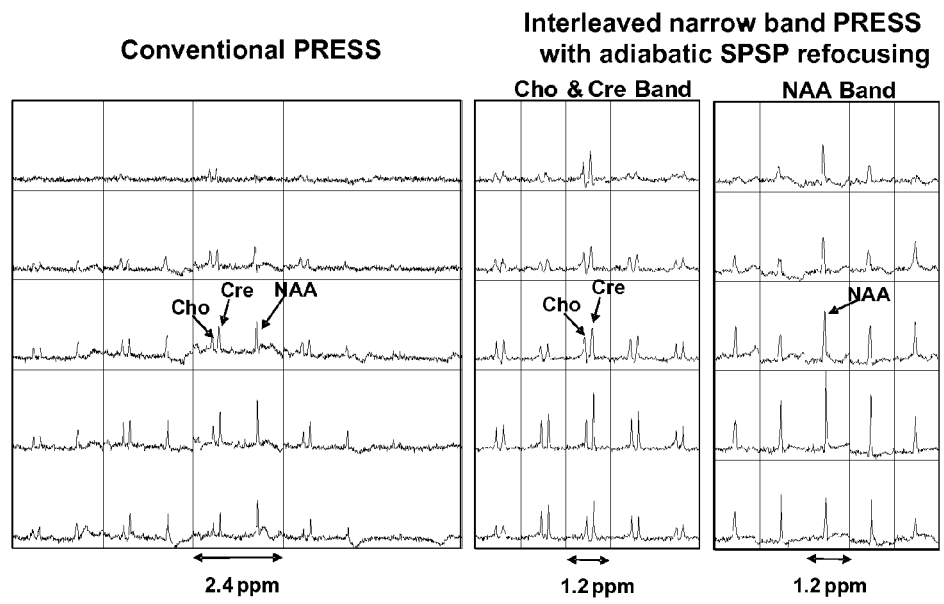
FIGS. 6D-E are spectral grids obtained using conventional PRESS and the interleaved narrow-band sequence.

The data obtained for the spectral grid location shown in FIG. 6A, using a standard PRESS sequence, can be seen in FIG. 6D. When the same region is excited using the interleaved narrow-band PRESS sequence with adiabatic SPSP refocusing pulses, the spectral grids for Cho, Cre and NAA shown in FIG. 6E are obtained. All spectra are plotted to the same vertical scale. Increased spatial coverage is clearly visualized.

In the spectra obtained using the standard PRESS sequence (FIG. 6D), non-central voxels, especially those in the anterior portion of the grid, have reduced overall signal due to severe $B_1$ drop-off. This reduction in $B_1$ is visible in the 2D $B_1$ profile shown in FIG. 6B. The interleaved narrow-band PRESS provides much more signal in these areas (FIG. 6E). The SPSP 90° pulse is still not adiabatic and shading due to the $B_1$ receive profile still exists, so some signal loss due to $B_1$ inhomogeneity is to be expected. For the standard PRESS sequence (FIG. 6D), the column of voxels along the left (i.e. patient's left, reader's right) edge of the PRESS box contain almost no NAA signal due to chemical shift localization error. This is considerably improved in the interleaved narrow-band acquisition (FIG. 6C). When all voxels are averaged, the overall signal increase obtained with our sequence, relative to standard PRESS, is approximately 70% for Cho+Cre and 110% for NAA.

It is important to note that to remain under peak RF amplifier limits and within SAR constraints, the 180° refocusing pulses in the conventional PRESS sequence are replaced by 137° pulses. This is the standard GE Healthcare implementation for PRESS sequences at 3 T and above, and involves a trade-off between signal amplitude and pulse bandwidth. High bandwidths are needed to reduce chemical shift misregistration errors. The adiabatic SPSP pulses used in the interleaved narrow-band sequence provide a 180° flip angle while remaining below RF peak amplifier and SAR limits, even when overdriven. As seen in FIG. 4C, chemical shift localization error is negligible, regardless of the flip angle. The sequence in this embodiment of the invention results in approximately 55% more signal than conventional PRESS at the central voxels due to this difference in flip angle as well as some $B_1$ inhomogeneity.

DISCUSSION AND CONCLUSIONS

An embodiment of the invention provides a 7 T $^1$H MRSI sequence that utilizes a SPSP excitation pulse and two narrow-band adiabatic SPSP refocusing pulses to achieve spectral coverage in an interleaved fashion. The sequence provides greater immunity to $B_1$ and $B_0$ variations and virtually eliminates chemical shift localization errors. In vivo data demonstrated that the interleaved narrow-band adiabatic SPSP sequence provides improved spatial coverage and increased overall SNR in comparison to a conventional PRESS sequence.

The interleaved spectral bands for this sequence are narrow enough to completely suppress water, eliminating the requirement for additional water suppression techniques. Furthermore, because the water resonance is not excited by any of the pulses in the metabolic interleaves, the sequence can easily be extended to incorporate a third spectral band centered at water to provide a signal for absolute quantification.

The 90° excitation pulse used in the sequence is not adiabatic and will thus induce some imaging shading due to $B_1$ variations. For example, a ±20% change in $B_1$ will result in approximately a 5% signal loss. Adiabatic alternatives for this pulse may be used so that excitation for all spectral bands can be made completely $B_1$-insensitive.

Partial fat suppression is also provided by the spectral selectivity of the SPSP pulses. Fat suppression techniques such as inversion recovery may be used with this sequence for further suppression of lipids resonating close to NAA. The sequence is geared toward imaging three of the main metabolites of interest in the brain (Cho, Cre, and NAA). A similar sequence with more interleaves and wider passbands may be use to capture other metabolites of interest.

Another embodiment of the invention may be use for multinuclear spectroscopy/spectroscopic imaging, especially for nuclei with spectra that contain a large chemical shift range, such as $^{13}$C. Metabolite resonances in the $^{13}$C spectrum are separated by many ppm, requiring very high bandwidth pulses to capture all peaks of interest without severe chemical shift localization error. By using an interleaved approach with several spectral bands centered at the metabolites of interest, pulses with narrower bandwidth may be used and chemical shift localization error reduced or even eliminated.

Generic Embodiment

Figure 7:
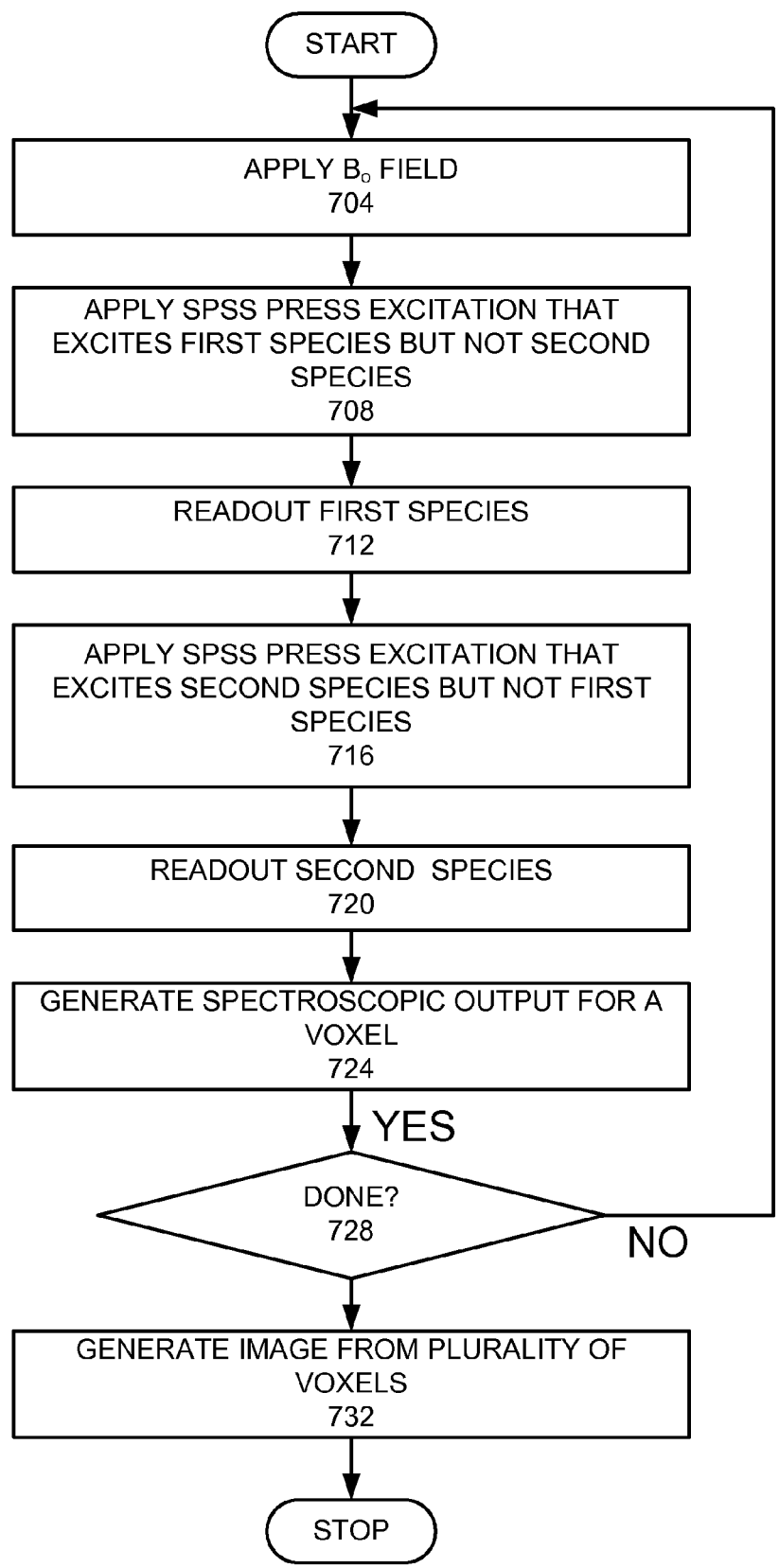
FIG. 7 is a high level flow chart of an embodiment of the invention.

FIG. 7 is a high level flow chart of a generalized embodiment of the invention. A $B_0$ field is applied (step 704). A first spatial-spectral (SPSP) position resolved spectroscopy sequence (PRESS) excitation with a sufficiently narrow band to excite a first species without exciting a second species is applied (step 708). Such a band should not be too narrow, otherwise the sequence will not be immune to $B_0$ shifts. A first readout that measures the first species is performed (step 712). A second SPSP PRESS excitation with a sufficiently narrow band to excite the second species without exciting the first species is applied (step 716). A second readout that measures the second species is performed (step 720). Spectroscopic data is generated for a portion of 2D k-space (i.e. spatial frequency space) (step 724). Steps 708 to 724 are repeated until spectroscopic output is generated for all k-space locations (step 728). A spectroscopic image is generated from the spectroscopic output for each of the k-space locations by applying a Fourier Transform in the spatial and spectral dimensions (step 732).

Figure 8:
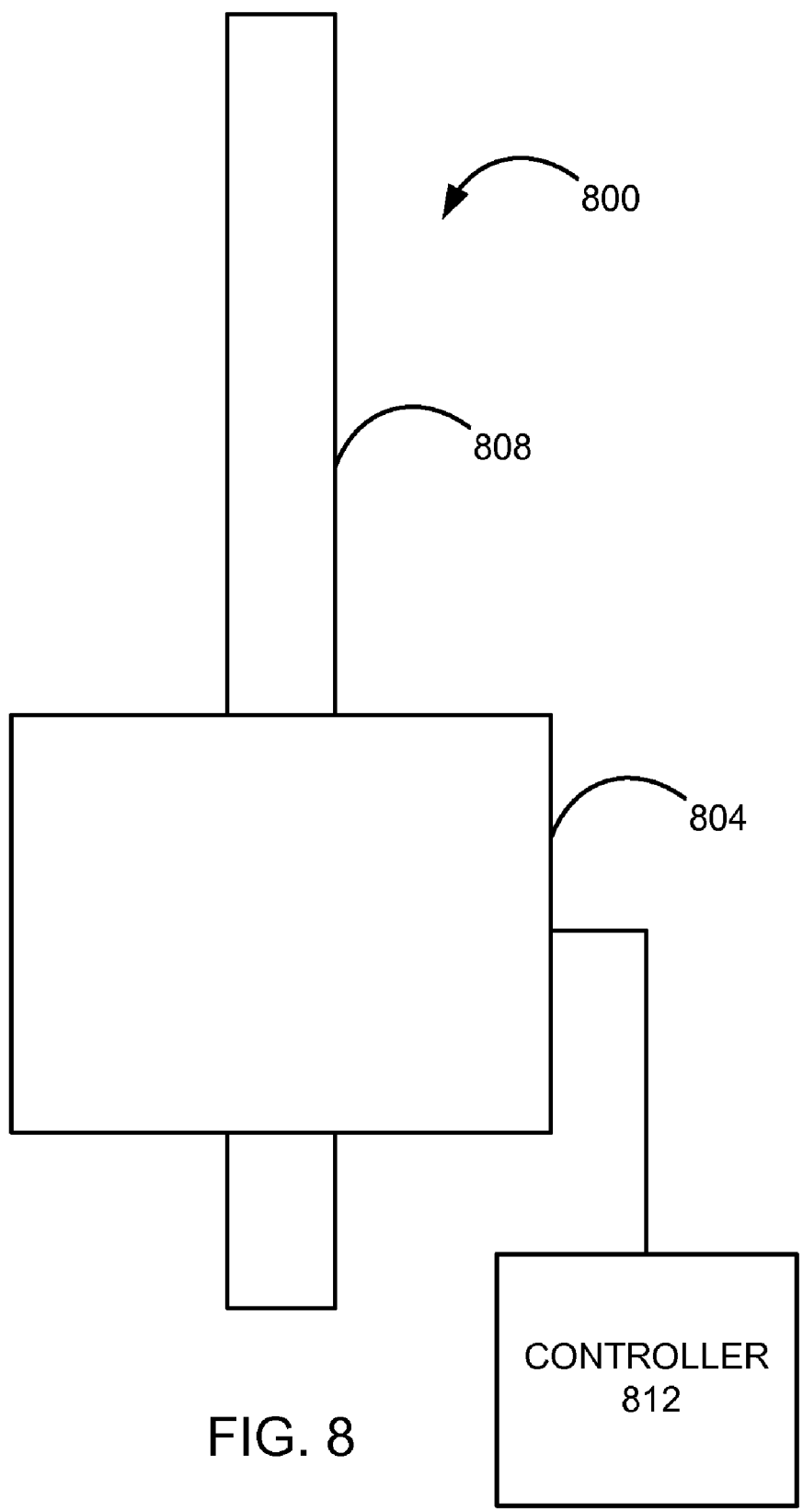
FIG. 8 is a schematic top view of a magnetic resonance imaging (MRI) system.

FIG. 8 is a schematic top view of a magnetic resonance imaging (MRI) system 800 that may be used in an embodiment of the invention. The MRI system 800 comprises a magnet system 804, a patient transport table 808 connected to the magnet system, and a controller 812 controllably connected to the magnet system. In one example, a patient would lie on the patient transport table 808 and the magnet system 804 would pass around the patient. The controller 812 would control magnetic fields including the radio frequency (RF) field provided by the magnet system 804 and would receive signals from detectors in the magnet system 804.

Figure 9A:
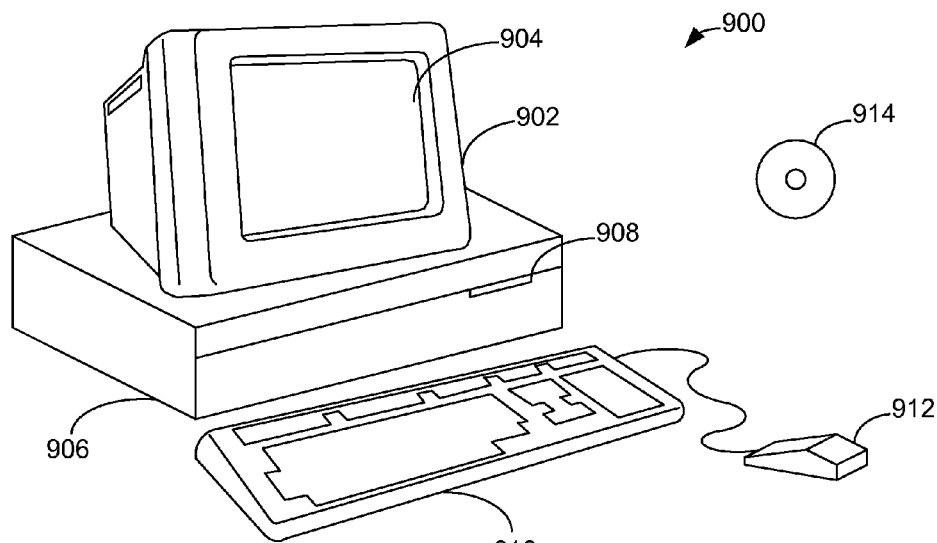
FIGS. 9A and 9B illustrate a computer system, which is suitable for implementing a controller used in embodiments of the present invention.
Figure 9B:
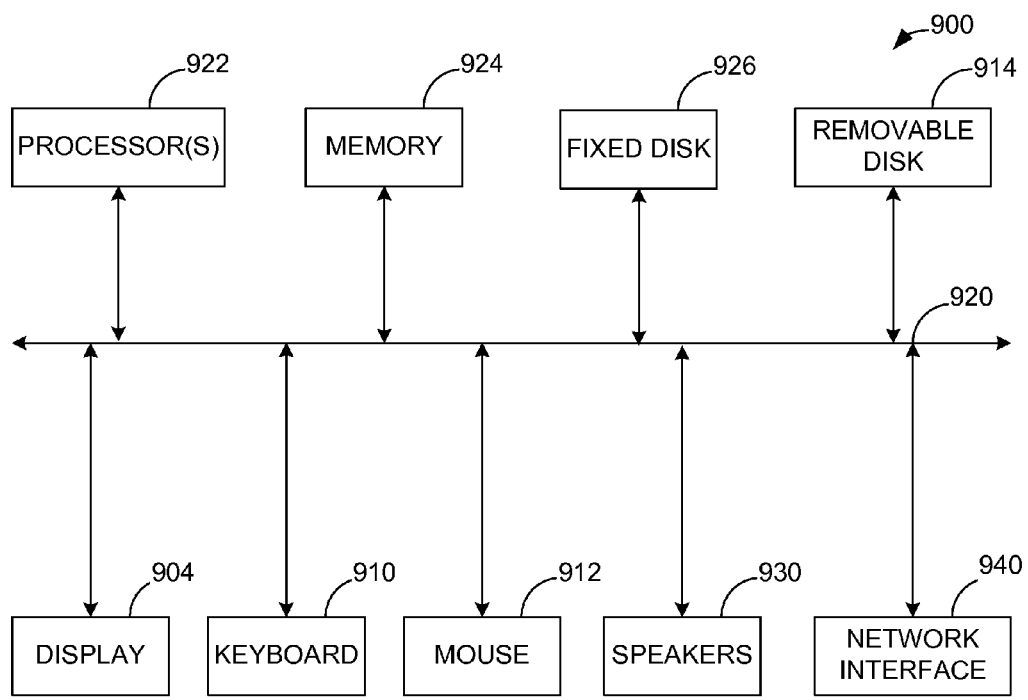

FIGS. 9A and 9B illustrate a computer system 900, which is suitable for implementing a controller 812 used in embodiments of the present invention. FIG. 9A shows one possible physical form of the computer system. Of course, the computer system may have many physical forms ranging from an integrated circuit, a printed circuit board, and a small handheld device up to a huge super computer. Computer system 900 includes a monitor 902, a display 904, a housing 906, a disk drive 908, a keyboard 910, and a mouse 912. Disk 914 is a computer-readable medium used to transfer data to and from computer system 900.

FIG. 9B is an example of a block diagram for computer system 900. Attached to system bus 920 are a wide variety of subsystems. Processor(s) 922 (also referred to as central processing units, or CPUs) are coupled to storage devices, including memory 924. Memory 924 includes random access memory (RAM) and read-only memory (ROM). As is well known in the art, ROM acts to transfer data and instructions uni-directionally to the CPU and RAM is used typically to transfer data and instructions in a bi-directional manner. Both of these types of memories may include any suitable of the computer-readable media described below. A fixed disk 926 is also coupled bi-directionally to CPU 922; it provides additional data storage capacity and may also include any of the computer-readable media described below. Fixed disk 926 may be used to store programs, data, and the like and is typically a secondary storage medium (such as a hard disk) that is slower than primary storage. It will be appreciated that the information retained within fixed disk 926 may, in appropriate cases, be incorporated in standard fashion as virtual memory in memory 924. Removable disk 914 may take the form of the computer-readable media described below.

CPU 922 is also coupled to a variety of input/output devices, such as display 904, keyboard 910, mouse 912, and speakers 930. In general, an input/output device may be any of: video displays, track balls, mice, keyboards, microphones, touch-sensitive displays, transducer card readers, magnetic or paper tape readers, tablets, styluses, voice or handwriting recognizers, biometrics readers, or other computers. CPU 922 optionally may be coupled to another computer or telecommunications network using network interface 940. With such a network interface, it is contemplated that the CPU might receive information from the network, or might output information to the network in the course of performing the above-described method steps. Furthermore, method embodiments of the present invention may execute solely upon CPU 922 or may execute over a network such as the Internet in conjunction with a remote CPU that shares a portion of the processing.

In addition, embodiments of the present invention further relate to computer storage products with a computer-readable medium that has computer code thereon for performing various computer-implemented operations. The media and computer code may be those specially designed and constructed for the purposes of the present invention, or they may be of the kind well known and available to those having skill in the computer software arts. Examples of computer-readable media include, but are not limited to: magnetic media such as hard disks, floppy disks, and magnetic tape; optical media such as CD-ROMs and holographic devices; magneto-optical media such as floptical disks; and hardware devices that are specially configured to store and execute program code, such as application-specific integrated circuits (ASICs), programmable logic devices (PLDs) and ROM and RAM devices. Examples of computer code include machine code, such as produced by a compiler, and files containing higher level code that are executed by a computer using an interpreter. Computer readable media may also be computer code transmitted by a computer data signal embodied in a carrier wave and representing a sequence of instructions that are executable by a processor.

An embodiment of the invention may be used to perform spectroscopy on a single voxel. Another embodiment of the invention may be used to perform spectroscopy on a grid of voxels: The sequence may be used in any organ (e.g. prostate and breast. In this embodiment, the spectral bands may center on metabolites other than Cho, Cre and NAA.

In other embodiments, a third SPSP PRESS excitation may be interleaved with the first and second SPSP PRESS excitations to selectively excite another species without exciting the first and second species.

In other embodiments each SPSP PRESS excitation may be used to excite more than one species.

Although an above example uses a Cartesian k-space trajectory with a two dimensional Fourier transform, a non-Cartesian trajectory could be used.

While this invention has been described in terms of several preferred embodiments, there are alterations, permutations, modifications and various substitute equivalents, which fall within the scope of this invention. It should also be noted that there are many alternative ways of implementing the methods and apparatuses of the present invention. It is therefore intended that the following appended claims be interpreted as including all such alterations, permutations, modifications, and various substitute equivalents as fall within the true spirit and scope of the present invention.

What is claimed is:

1. A method for performing spectroscopy using an interleaved readout for at least two species, comprising of:
   a) applying a $B_0$ field;
   b) applying a first spatial-spectral (SPSP) position resolved spectroscopy sequence (PRESS) excitation with a sufficiently narrow band to excite a first species without exciting a second species;
   c) performing a first readout that measures the first species;
   d) applying a second SPSP PRESS excitation with a sufficiently narrow band to excite the second species without exciting the first species;
   e) performing a second readout that measures the second species; and
   f) generating a spectroscopic output for a portion of k-space from the first readout and the second readout, wherein steps b-e are performed a plurality of times so that the first SPSP PRESS excitation is interleaved with the second SPSP PRESS excitation.

2. The method of claim 1, wherein the spectroscopic output is a spectrum for the first species and the second species.

3. The method of claim 1, wherein the spectroscopic output is a spectroscopic image for the first species and the second species from the first and second readouts.

4. The method of claim 3, wherein the applying a first spatial-spectral (SPSP) position resolved spectroscopy sequence (PRESS) excitation excites a third species, wherein the first readout measures the third species and the spectroscopic image also shows the third species.

5. The method of claim 4, wherein the first SPSP PRESS excitation comprises:
a SPSP 90° pulse;
a first adiabatic SPSP 180° pulse; and
a second adiabatic SPSP 180° pulse, wherein the SPSP 90° pulse and the first and second adiabatic SPSP 180° pulses each have a spectral profile centered on the resonant frequency for exciting the first and third species and a bandwidth sufficiently narrow to avoid exciting the second species; and
wherein the second SPSP PRESS excitation comprises:
a SPSP 90° pulse;
a first adiabatic SPSP 180° pulse; and
a second adiabatic SPSP 180° pulse, wherein the SPSP 90° pulse and the first and second adiabatic SPSP 180° pulses each have a spectral profile centered on the resonant frequency for exciting the second species and a bandwidth sufficiently narrow to avoid exciting the first and third species.

6. The method of claim 5, wherein each SPSP 90° pulse has a same spectral profile as the associated first and second adiabatic SPSP 180° pulses.

7. The method of claim 6, wherein the first species is choline containing compounds, the second species is N-acetyl aspartate, and the third species is creatine/phosphocreatine.

8. The method of claim 7, wherein the first and second adiabatic SPSP 180° pulses for the first excitation and the second excitation were designed by first creating an adiabatic sech/tanh pulse wherein the amplitude A(t) of the adiabatic sech/tanh pulse is $A(t) = A_0 \mathrm{sech}(\beta t) - T/2 \leq t \leq T/2$ and wherein the frequency modulation function $\Delta\omega(t)$ of the adiabatic sech/tanh pulse is $\Delta\omega(t) = -\mu\beta\tanh(\beta t) - T/2 \leq t \leq T/2$ where $\beta$ is a modulation angular frequency, $\mu$ is a modulation angular frequency, and T is a pulse duration.

9. The method of claim 8, further comprising:
a third SPSP PRESS excitation with a sufficiently narrow band to excite a fourth species without exciting the first, second, and third species, and wherein the first and second SPSP PRESS excitations do not excite the fourth species; and
performing a third readout that measures the fourth species.

10. The method of claim 4, wherein the first species is choline containing compounds, the second species is N-acetyl aspartate, and the third species is creatine/phosphocreatine.

11. The method of claim 1, wherein the first and second readouts are used to generate spectroscopic outputs for a 2D grid in k-space, and further comprising using the spectroscopic outputs for a 2D grid in k-space to generate, through the use of a Fourier Transform, a spectroscopic image containing spectra from a plurality of voxels.

12. The method of claim 1, wherein the first SPSP PRESS excitation comprises:
a SPSP 90° pulse;
a first adiabatic SPSP 180° pulse; and
a second adiabatic SPSP 180° pulse, wherein the SPSP 90° pulse and the first and second adiabatic SPSP 180° pulses each have a spectral profile centered on a resonant frequency for exciting the first species and a bandwidth sufficiently narrow to avoid exciting the second species; and
wherein the second SPSP PRESS excitation comprises:
a SPSP 90° pulse;
a first adiabatic SPSP 180° pulse; and
a second adiabatic SPSP 180° pulse, wherein the SPSP 90° pulse and the first and second adiabatic SPSP 180° pulses each have a spectral profile centered on a resonant frequency for exciting the second species and a bandwidth sufficiently narrow to avoid exciting the first species.

13. The method of claim 12, wherein each SPSP 90° pulse has a same spectral profile as the associated first and second adiabatic SPSP 180° pulses.

14. The method of claim 1, further comprising:
a third SPSP PRESS excitation with a sufficiently narrow band to excite a third species without exciting the first and second species, and wherein the first and second SPSP PRESS excitations do not excite the third species; and
performing a third readout that measures the third species.

15. The method, as recited in claim 1, wherein the spectroscopic output comprises interleaved spectral bands, wherein the interleaving allows excitation of a large spectral range without increasing scan time.

16. A computer implemented method, comprising:
a) applying a $B_0$ field;
b) performing for a plurality of cycles:
applying a first spatial-spectral (SPSP) position resolved spectroscopy sequence (PRESS) excitation with a sufficiently narrow band to excite a first species without exciting a second species, wherein the first SPSP PRESS excitation comprises:
a SPSP 90° pulse;
a first adiabatic SPSP 180° pulse; and
a second adiabatic SPSP 180° pulse, wherein the SPSP 90° pulse and the first and second adiabatic SPSP 180° pulses each have a spectral profile centered on a frequency for exciting the first species and a bandwidth sufficiently narrow to avoid exciting the second species;
performing a first readout that measures the first species;
applying a second SPSP PRESS excitation with a sufficiently narrow band to excite the second species without exciting the first species, wherein the second SPSP PRESS excitation comprises:
a SPSP 90° pulse;
a first adiabatic SPSP 180° pulse; and
a second adiabatic SPSP 180° pulse, wherein the SPSP 90° pulse and the first and second adiabatic SPSP 180° pulses each have a spectral profile centered on a frequency for exciting the second species and a bandwidth sufficiently narrow to avoid exciting the first species; and
performing a second readout that measures the second species; and
c) generating a spectroscopic output for the first species and the second species by interleaving the first and second readouts.

17. The computer implemented method of claim 16, wherein the spectroscopic output is a spectrum for the first species and the second species.

18. The computer implemented method of claim 16, wherein the spectroscopic output is a spectroscopic image for the first species and the second species.

19. A magnetic resonance imaging apparatus, comprising:
a magnetic resonance imaging excitation and detection system; and
a controller electrically connected to the magnetic resonance imaging excitation and detection system, comprising:
a display; and
at least one processor configured for implementing a tangible computer readable media, comprising:
computer readable code for applying a $B_0$ field;
computer readable code for applying a first spatial-spectral (SPSP) position resolved spectroscopy sequence (PRESS) excitation with a sufficiently narrow band to excite a first species without exciting a second species;
computer readable code for performing a first readout that measures the first species;
computer readable code for applying a second SPSP PRESS excitation with a sufficiently narrow band to excite the second species without exciting the first species;
computer readable code for performing a second readout that measures the second species;
computer readable code for generating a spectroscopic image for the first species and the second species by interleaving the first and second readouts; and
computer readable code for displaying the spectroscopic image on the display.

20. The apparatus as recited in claim 19, wherein the magnetic resonance imaging excitation and detection system may be placed around a human head to allow the generation of a spectroscopic image of a brain.

* * * * *